United States Patent [19]
Winter et al.

[11] Patent Number: 5,555,880
[45] Date of Patent: Sep. 17, 1996

[54] HIGH FREQUENCY OSCILLATORY VENTILATOR AND RESPIRATORY MEASUREMENT SYSTEM

[75] Inventors: Dean C. Winter, San Antonio, Tex.;
Ralph E. Harris, Cary, N.C.; Kevin S. Honeyager, San Antonio, Tex.

[73] Assignee: Southwest Research Institute, San Antonio, Tex.

[21] Appl. No.: 190,322

[22] Filed: Jan. 31, 1994

[51] Int. Cl.$^6$ ........................................... A61M 16/00
[52] U.S. Cl. ................................. 128/204.21; 128/204.23
[58] Field of Search ........................ 128/204.18, 204.21, 128/204.23, 204.25

[56] References Cited

U.S. PATENT DOCUMENTS

| | | | |
|---|---|---|---|
| 3,410,264 | 11/1968 | Frederik . | |
| 3,726,271 | 4/1973 | Mondshine et al. . | |
| 4,224,940 | 9/1980 | Mannier | 128/204.25 |
| 4,265,237 | 5/1981 | Schwanbom et al. | 128/204.25 |
| 4,326,416 | 4/1982 | Fredberg | 128/720 |
| 4,333,476 | 6/1982 | Downing, Jr. | 128/720 |
| 4,417,573 | 11/1983 | De Vries | 128/204.25 |
| 4,425,805 | 1/1984 | Ogura et al. | 73/861.29 |
| 4,481,944 | 11/1984 | Bunnell | 128/204.25 |
| 4,565,194 | 1/1986 | Weerda et al. | 128/204.25 |
| 4,646,733 | 3/1987 | Stroh et al. | 128/204.25 |
| 4,719,910 | 1/1988 | Jensen | 128/204.21 |
| 4,747,402 | 5/1988 | Reese et al. | 128/204.21 |
| 4,747,403 | 5/1988 | Gluck et al. | 128/204.21 |
| 4,805,612 | 2/1989 | Jensen | 128/204.21 |
| 4,838,257 | 6/1989 | Hatch | 128/204.18 |
| 4,838,259 | 6/1989 | Gluck et al. | 128/204.25 |
| 4,976,154 | 12/1990 | Schneider et al. | 73/861.06 |
| 5,239,994 | 8/1993 | Atkins | 128/204.18 |
| 5,303,698 | 4/1994 | Tobia et al. | 128/204.25 |
| 5,307,794 | 5/1994 | Rauterkus et al. | 128/204.25 |

OTHER PUBLICATIONS

Kamm, R. D., Slutsky, A. S., Drazen, J. M., High–Frequency Ventilation, CRC Critical Reviews in Biomedical Engineering, vol. 9, Issue 4, pp. 347–380, 1984.

Bohn, D. J., Miyasaka, K., Marchak, B. E., Thompson, W. K., Roese, A. B. and Bryan, A. C., Ventilation By High–Frequency Oscillation, J. Appl. Physiol., vol. 48, Issue 4, pp. 710–716, 1980.

HIFI Study Group, High–Frequency Oscillatory Ventilation Compared With Conventional Mechanical Ventilation In The Treatment of Respiratory Failure in Preterm Infants: Assessment Of Pulmonary Function At 9 Months of Corrected Age, N. England J. Med, vol. 116, No. 6, pp. 933–941, 1989.

Gerstmann, D.R., Delemos, R. A., Coalson, J. J., Clark, R. H., Wiswell, T. E., Winter, D. C., Kuehl, T. J., Meredith, K. S. and Null, Jr., D. M., Influence of Ventilatory Technique On Pulmonary Baroinjury in Baboons With Hyaline Membrane Disease, Pediatric Pulmonology, 5:82–91, pp. 82–91, 1988.

Delemos, R. A., Coalson, J. J., Gerstmann, D. R., Null, Jr., D. M., Ackerman, N. B., Escobedo, M. B., Robotham, J. L. and Kuehl, T. J., Ventilatory Management of Infant Baboons With Hyaline Membrane Disease: The Use Of High Frequency Ventilation, Pediatric Research, vol. 21, No. 6, pp. 594–602, 1987.

Gerstmann, D. R., Fouke, J. M., Winter, D. C., Taylor, A. F. and Delemos R. A., Proximal, Tracheal, and Alveolar Pressures During High–Frequency Oscillatory Ventilation In a Normal Rabbit Model, Pediatric Research, vol. 28 No. 4, pp. 367–373, 1990.

Chang, H. K. and Mortola, J. P., Fluid Dynamic Factors In Tracheal Pressure Measurement, J. Appl. Physiol., vol. 51, Issue 1, pp. 218–225, 1981.

Wegner, C. D., Jackson, A. C., Berry, J. D. and Gillespie, J. R., Dynamic Respiratory Mechanics In Monkeys Measured By Forced Oscillations, Respiration Physiology, vol. 55, pp. 47–61, 1984.

Clement, J., Bobbaers, H., Schepers, R. and Van De Woestijne, K. P., Pulmonary Resistance And Compliance By Auto– and Cross–Correlation Functions Of Transpulmonary Pressure And Flow, J. Appl. Physiol., vol. 57, Issue 5, pp. 1448–1453, 1984.

Seybert, A. F. and Ross, D. F., Experimental Determination Of Acoustic Properties Using A Two–Microphone Random–Excitation Technique, J. Acoust. Soc. Am., vol. 61, No. 5, pp. 1362–1370, 1977.

To, C. W. S. and Doige, A. G., A Transient Testing Technique For The Determination of Matrix Parameters Of Acoustic Systems, I: Theory And Principles, Journal Of Sound and Vibration, vol. 62, No. 2, pp. 207–222, 1979.

To, C. W. S. and Doige, A. G., A Transient Testing Technique For The Determination of Matrix Parameters Of Acoustic Systemns, II: Experimental Procedures And Results, Journal Of Sound And Vibration, vol. 62, No. 2, pp. 223–233, 1979.

*Primary Examiner*—Aaron J. Lewis
*Attorney, Agent, or Firm*—Akin, Gump, Strauss, Hauer & Feld, L.L.P.

[57] ABSTRACT

A high frequency oscillatory ventilator for infants and adults using feedback control to maintain either the desired tidal volume or pressure delivered to the subject. The inspiratory to expiratory time ratio of the ventilator is variable. The ventilator corrects the measured pressure for arbitrarily-sized endotracheal tubes and calculates the actual pressure or tidal volume delivered to the subject. The ventilator also separates the source of the tidal volume oscillations from the patient circuit with a flexible membrane or diaphragm, allowing transmission of oscillating tidal volumes while blocking mean airway pressures. The patient circuit is flexible, but fabricated from low-compliance material to minimize the loss of tidal volume. The ventilator uses feedback control of the exhaust flow to maintain mean airway pressure in the presence of an independently controlled bias flow. Further, a respiratory impedance measurement system is built into or connected to the patient circuit which monitors changes in lung mechanics while the patient is connected to the high frequency ventilator without changing mean airway pressure or removing the patient from the ventilator.

25 Claims, 4 Drawing Sheets

HIGH FREQUENCY OSCILLATORY VENTILATOR AND RESPIRATORY MEASUREMENT SYSTEM

FIELD OF INVENTION

Background of the Invention

When assistance is needed in breathing, such as when the lung is injured or diseased or when thoracic surgery is performed, mechanical positive pressure ventilators are often used. Conventional mechanical ventilators (CMVs) operate at stroke or tidal volumes and frequencies that approximate normal breathing patterns. The tidal volume is essentially defined as the difference between end inspiratory and end expiratory volumes. CVMs can cause a variety of problems, most notably pulmonary barotrauma or injury to the lung due to high pressure and overdistension.

Several years ago, a new method of ventilation was discovered in which small tidal volumes delivered at supraphysiologic frequencies were shown to provide adequate gas exchange in the lung. Several different types of these ventilators were developed all classified under the name of high frequency ventilation (HFV). High frequency oscillatory ventilation (HFOV) differs from other types of HFV in that HFOV incorporates an active exhalation phase in the ventilator and operates at frequencies as high as 30 Hz and tidal volumes as small as $\frac{1}{10}$ that delivered by CMV. The active exhalation phase and smaller tidal volumes of HFOV have been seen as important attributes.

HFV has been used primarily to support prematurely born infants. Several high frequency ventilators have become commercially available, while others are being developed, although most or all of these ventilators are intended for infants. While the general experience with HFV in infants has been mixed, researchers and physicians have been very successful in using HFOV to support infants born prematurely and to prevent or moderate the chronic lung injury often associated with prematurity. Several types of adult lung injury such as smoke inhalation, or other lung diseases such as adult respiratory distress syndrome (ARDS) are pathologically and functionally similar to infant lung injury. ARDS is an area of particular interest since this disease is a leading cause of death, second only to lung cancer among respiratory diseases.

Design limitations have been a major factor in limiting the use of HFOV to infants. The primary problem of using HFOV in adults has been providing enough tidal volume for adults, while keeping the ventilator reasonably small and quiet. This has not been a matter of simply scaling infant HFOVs to handle adults, since the scaling factor is non-linear. HFOVs with the power to ventilate adults have been too large and noisy to be of practical use.

Reduced to their primary subsystems, ventilators can be functionally reduced to a pump or pneumatic system that generates a tidal volume which is delivered through a patient circuit to the patient or subject. There is an inlet for the delivery of fresh gas and an outlet for the exhausting of exhaled gas. An endotracheal tube connects the patient circuit to the subject so that gas passes between the subject's main airway, the trachea, and the ventilator.

The effect of the compliance of the patient circuit connecting the subject to the ventilator on the tidal volume is one problem associated with HFV. For CMV the compliance is of little or no consequence to the delivered tidal volume. However, during HFV, even with relatively low compliance tubing, it has been found that as much as 98% of the tidal volume may not be delivered to the subject, but instead is absorbed in expansion of the circuit tubing or compression of the gas in the circuit.

A second problem is that HFVs of prior art have not been able to accurately measure delivered tidal volume because no adequate method had been found. Suitable flow meters have not been developed that can measure the intermittent, oscillating, humidified and often blood and mucus contaminated air delivered by ventilators or removed from the lungs on the exhalation cycle. Screens or orifices that might be used to create a measurable pressure drop proportional to flow are unacceptable because they become rapidly clogged with mucus, blood or secretions. Ultrasonic flow meters have been tried, such as the flow meters provided on some ventilator models produced by Bear Medical Corporation, but have generally proved to be inaccurate at low flows or in the presence of changes in gas composition, temperature or humidity.

Even if a piston is used for air displacement, air compressibility and other artifacts prevent the computation of tidal volume from piston displacement. The ability to measure tidal volume in either conventional or high frequency pressure limited ventilators, would be a significant advancement in clinical monitoring, and would provide the physician with important information for patient management.

Ventilators are classified as either as pressure-cycled or volume-cycled, depending on whether they are limited by delivered pressure or tidal volume, respectively. All known conventional and high frequency neonatal ventilators of prior art are pressure-cycled ventilators. The pressure is measured in the patient circuit on the ventilator side of the endotracheal tube. Ideally, the measured pressure should reflect the airway pressure, which is the pressure delivered to the subject.

Clinically, it is desirable to measure both tidal volume and delivered pressure, even though only one variable can be independently controlled. In current HFOVs, however, not only is tidal volume not measured but the measurement of the independent variable, which is delivered pressure, often contains significant errors. These errors are due to the endotracheal tube which acts as a nonlinear, acoustic low pass filter and significantly attenuates the pressure waveform at the frequencies used during HFV. In addition, flow nonlinearities, such as boundary layer separation, can lead to losses in mean pressure between the endotracheal tube and the airways. Therefore, both the mean and peak pressure can be significantly altered, so that the pressure measured in the patient circuit may be and often has been very different from the pressure actually delivered to the subject. Even endotracheal tubes with pressure ports at their distal end do not accurately measure airway pressures during HFV.

A third problem is due to the requirement for an "open" patient circuit so that fresh gas can enter the system and exhaled gas can be removed. This has been shown in HFV to result in a significant loss of ventilation volume to the atmosphere.

A fourth problem is that the changing mechanical state of the respiratory system cannot be assessed while the subject is on HFV. The mechanical state concerns the mechanical properties of the respiratory system, which includes the respiratory resistance and compliance as well as other more sophisticated measures of mechanical components of the lung. In both injured infants and adults, the changes in the clinical state of the subject are often reflected in changes in mechanical properties of the respiratory system. Conventional pulmonary function tests which assess the mechanical state are being incorporated into the newer CMVs. However, the efficacy of HFOV depends on maintaining the mean airway pressure, which means that conventional pulmonary function tests cannot be used. Nevertheless, it is important and desirable to track changes in the mechanical status of the respiratory system during HFV to maintain optimal ventilator settings and to minimize hazards from high pressures.

A fifth problem is the generation of oscillating tidal volumes in the presence of a mean pressure in the patient circuit. Whether the oscillating tidal volume is generated mechanically by a moving piston or pneumatically, a mean pressure represents a preload that must be overcome. This has increased the power requirements of ventilators and has reduced their efficiency.

SUMMARY OF INVENTION

A high frequency oscillatory ventilator (HFOV) according to the present invention is disclosed which addresses and solves many of the problems associated with ventilators known heretofore thus providing an HFOV system that can be used for both infants and adults. Experience has shown that it is useful to control the shape of the tidal volume waveform at different times on the same subject. It has also been shown that to prevent an inadvertent build-up of pressure in the lung, it is important to have a variable ratio of the inspiratory to expiratory time, otherwise referred to as the I:E ratio. The volume or pressure cycled ventilator according to the present invention uses feedback control to maintain either the desired tidal volume or pressure amplitude delivered to the subject. The I:E ratio of the ventilator of the present invention is variable, and the waveform generated by the ventilator can be arbitrarily controlled.

The ventilator includes a patient circuit pressure measurement system which corrects the measured pressure for the presence of an arbitrary-size of endotracheal tube and calculates the actual pressures delivered to the subject. The HFOV of the present invention incorporates a method to separate the source of the tidal volume oscillations from the patient circuit by the use of a flexible diaphragm or membrane, allowing the transmission of oscillating tidal volumes but blocking the transmission of mean airway pressures. The patient circuit is flexible, but fabricated from rigid or low-compliance material to minimize the loss of volume delivered to the patient.

The HFOV according to the present invention includes a mean airway pressure system which uses feedback control of the exhaust flow to maintain mean airway pressure in the presence of an independently controlled bias flow. Further, a respiratory impedance measurement system is built into or connected to the patient circuit which monitors changes in lung mechanics while the patient is connected to the high frequency ventilator without changing mean airway pressure or removing the patient from the ventilator.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
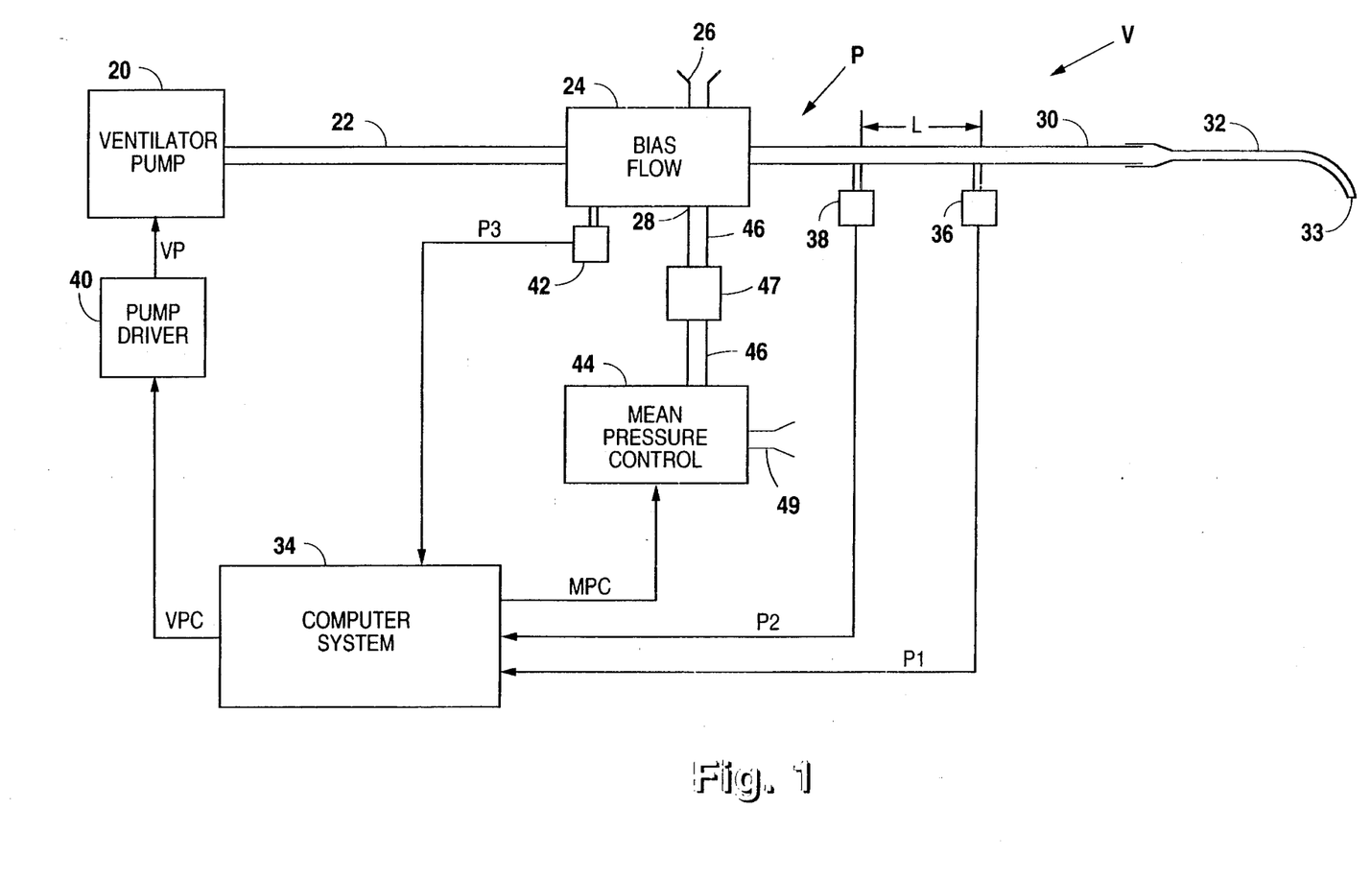
FIG. 1 is a simplified block diagram of a high frequency oscillatory ventilator according to the present invention.

Referring now to FIG. 1, a simplified block diagram of a high frequency oscillatory ventilator (HFOV) according to the present invention is shown, which will generally be referred to by the letter V. In general, a ventilator air pump 20 is provided which generates a relatively small tidal volume at the desired frequencies to a patient circuit, generally referred to by the letter P, which delivers the tidal volume to the patient or subject requiring breathing assistance. The frequency of ventilation is preferably between 5 and 15 Hertz (Hz), but could be as high as 30 Hz or more. A suitable hose or pipe 21 (FIG. 4) is connected between the ventilator pump 20 and a water trap section 140 which is part of the patient circuit P. The patient circuit P preferably includes a rigid or non-compliant tube 22 coupled between the water trap section 140 and a bias flow section 24.

The bias flow section 24 includes a bias flow inlet 26 which provides a fresh supply of air, and also includes an exhaust outlet 28. The bias flow inlet 26 includes a valve (not shown) so that the flow of fresh air provided can be independently controlled. A preferably non-compliant or rigid tube 30 is connected between the bias flow section 24 and an endotracheal tube 32 including an outlet 33 through which gases pass between the subject's main airway, the trachea, and the ventilator V. The endotracheal tube 32 could be of various sizes, shapes and materials as known to those skilled in the art. In this manner, the patient circuit P could generally be characterized as a tube comprising the tubes 22 and 30 including a bias flow section 24 attached along the tube for providing fresh gas and for exhausting exhaled gas, and an endotracheal tube 32 attached at one end of the tube.

In the preferred embodiment of the ventilator V, a computer 34 is provided to control the ventilator V, to allow an operator to set the level of certain measured parameters such as the mean pressure within the patient circuit P, to determine the controlled variable of the feedback control circuit which is either the delivered pressure or tidal volume, and to control the ventilator pump 20 based on the controlled variable. A flow meter pressure transducer 36 is provided and is preferably attached to the tube 30 relatively near the endotracheal tube 32 and measures the pressure in the tube 30 which approximates the delivered pressure to the subject intubated by the endotracheal tube 32.

The pressure transducer 36 preferably converts the measured pressure to a proportional voltage signal P1 which is provided to the computer 34. The computer 34 receives the voltage signal P1 from the pressure transducer 36 and controls the ventilator pump 20 by a signal VPC connected to a pump driver 40, which provides a signal VP to the ventilator pump 20. In this manner, the computer 34 can control the ventilator pump 20 to maintain the pressure in the tube 30 as measured by the pressure transducer 36, approximately the delivered pressure to the subject.

The ventilator V could operate satisfactorily using only the pressure transducer 36 mounted on the tube 30, although the measured pressure only approximates the pressure delivered to the subject and may contain significant errors due to the endotracheal tube 32 which acts as an acoustic low pass filter, and thus may significantly attenuate the actual delivered pressure at the end of the endotracheal tube 32 to the subject. Furthermore, delivered tidal volume may not be determined with only the one pressure transducer 36. Thus, another pressure transducer 38 is preferably mounted on the tube 30 at a predetermined length L from the pressure transducer 36. The pressure transducer 38 operates similarly to the pressure transducer 36, measuring the pressure and preferably converting the measured pressure to a proportional voltage signal P2 which is provided to the computer system 34. As will be further described below, the computer system 34 can calculate more precisely the tidal volume and pressure delivered to the subject by the endotracheal tube 32 derived from the pressure measurements of the pressure transducers 36 and 38.

A second feedback control circuit is used to maintain the mean pressure, sometimes referred to as the mean airway pressure, within the patient circuit P. A pressure transducer 42 is connected to the bias flow section 24 which measures the pressure in the bias flow section 24 of the patient circuit P and preferably converts this pressure to a proportional voltage signal P3 which is provided to the computer 34. The mean airway pressure in the patient circuit P is controlled by a mean pressure control system 44, which is connected to the exhaust outlet 28 of the bias flow section 24 through a series of cavities 47 and tubes 46 which generally function as an acoustic low-pass filter. The cavities 47 preferably includes one or two capacitive tanks (not shown). This "filter" minimizes the transmission of oscillations from the mean pressure control system 44 to the patient circuit P, and also minimizes the loss of tidal volume oscillations through the exhaust 28. The gas exhaled by the subject are expelled through an exhaust 49 of the mean pressure control system 44. The computer 34 controls the mean pressure control system 44 through a signal MPC so that the computer 34 controls the mean airway pressure in the patient circuit P to maintain a predetermined level of the mean pressure as set by an operator of the computer 34. Note that the pressure transducer 42 could be fashioned to measure the mean airway pressure or, preferably, simply the pressure within the bias flow section 24. In the latter case, the computer system 34 maintains the mean pressure in the patient circuit P by monitoring the pressure over time.

Figure 2:
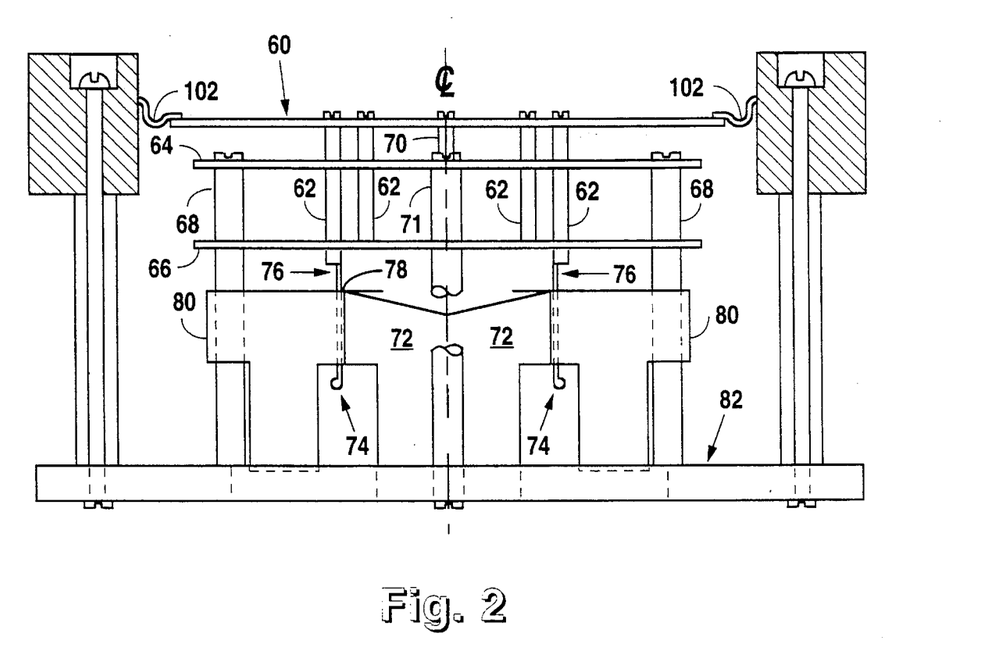
FIG. 2 is a partial cross-sectional diagram of a piston, magnet and coil assembly which is part of a ventilator pump used in the ventilator of FIG. 1.

Referring now to FIG. 2, a partial cross-sectional diagram of a piston, magnet and coil assembly is shown which is part of the ventilator pump 20. The ventilator pump 20 is designed and operates in a similar manner as a loudspeaker, and preferably includes a piston 60 which is axially oscillated by an electromagnet coil and magnet system. The piston 60 is preferably a round, flat piece of aluminum tapered towards its outer edges (FIG. 3) to reduce weight and increase strength. The piston 60 is also preferably bolted or otherwise connected using multiple supports or bolts 62 to a spider assembly including an upper spider 64 and a lower spider 66. The spiders 64 and 66 preferably are flexible, relatively flat pieces of fiberglass attached to the bolts 62 and supported towards their outer ends by column supports 68. The column supports 68 hold the spiders 64 and 66 parallel with respect to each other and to the piston 60, spaced a distance apart below the piston 60. An armature coil 76 is located below the lower spider 66 and attached to the spider assembly by the bolts 62. In this manner, the piston 60 and the armature coil 76 may move up and down thereby flexing the spiders 64 and 66 up and down, respectively. The spiders 64 and 66 resist torsion thereby providing a resting position as shown in FIG. 2 when the spiders 64 and 66 are not flexed.

The armature coil 76 is inserted into a circular slot 78 formed through the center of a circular T-shaped magnet 80. The magnet 80 and the column supports 68 are mounted on a steel plate 82. A metal center support 70 is attached near the center of the piston 60 slidably mounted within a cylindrical metal column 71 which is positioned within a center hole of the magnetic center core 72 and connected to the steel plate 82. The armature coil 76 slidably moves up and down relative to the metal column 71 as the piston 60 moves. The pump driver 40 comprises a current amplifier having an input for receiving the VPC signal from the computer 34 and an output providing the VP signal to the coil 74. Thus, the pump driver 40 varies the current through the windings of the coil 74 within the magnetic field established by the magnet 80, the column 72 providing a magnetic center pole and the steel plate 82 providing a magnetic rear pole, which varies the forces applied to the piston 60 so that it moves axially in response to the current in the coil 74. This allows the production of an arbitrary stroke volume waveform within the response limits of the assembly of the ventilator pump 20. It also allows control of the variable ratio of the inspiratory to expiratory time (I:E) ratio as easily programmable using the computer 34. The piston 60 is typically driven by a waveform on the VP signal composed of single or multiple sinuosity as controlled by the computer 34.

Figure 3:
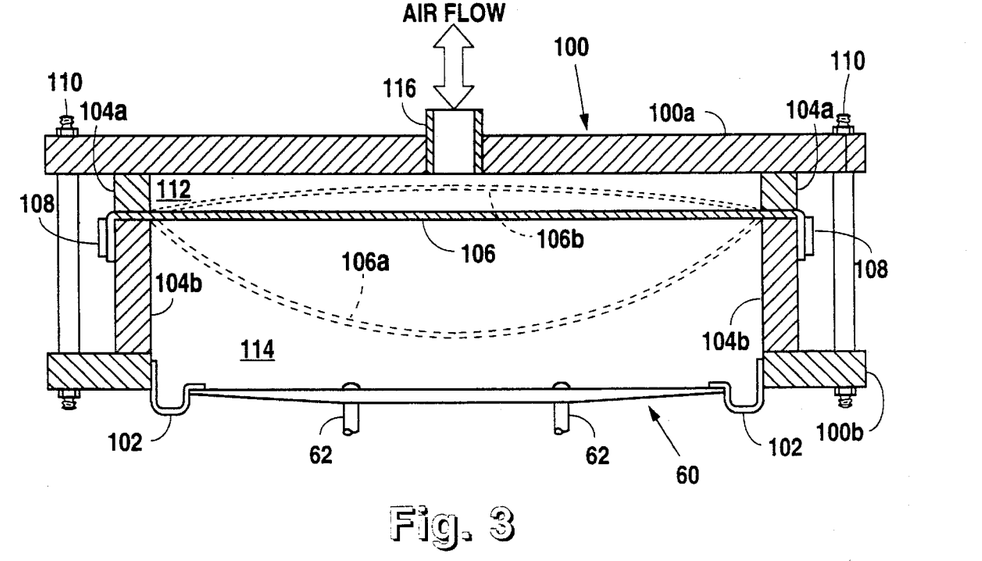
FIG. 3 is a partial cross-sectional diagram of a piston, cylinder and diaphragm assembly of the ventilator pump of FIG. 1.

Referring now to FIG. 3, a partial cross-sectional diagram of a piston, cylinder and diaphragm assembly of the ventilator V is shown. The piston 60 interfaces with an airpump cylinder closure 100 through a rolling seal 102, allowing the piston 60 to move relative to the closure 100 with limited loss of air. The closure 100 includes a closure head 100a, a closure base 100b and cylinder walls including an upper cylinder wall 104a integrally formed with the closure head 100a, and a lower cylinder wall 104b integrally formed with the closure base 100b. One end of the rolling seal 102 is glued or otherwise fastened to the upper side of the piston 60. The other end of the rolling seal 102 is glued or otherwise fastened to the lower cylinder wall 104b or the closure base 100b.

A flexible membrane or diaphragm 106 covers and is fastened to the upper end of the lower cylinder wall 104b using a diaphragm clamp 108. The diaphragm 106 is preferably composed of latex, but could be composed of a suitable equivalent material. The closure head 100a and the closure base 100b are bolted together with retainer bolts 110 so that the upper and lower cylinder walls 104a and 104b couple together on either side of the diaphragm 106 forming an upper cavity 112 between the diaphragm 106 and the closure head 100a, and a lower cavity 114 between the piston 60 and the diaphragm 106. The closure head 100a has an outlet 116 formed preferably near its center through which gas or air from the patient circuit P can communicate with the cavity 112. One end of the hose 21 fastens to the outlet 116 for communication of the tidal volume cycles to the patient circuit P as generated by the piston 60.

The rolling seal 102 and piston 60 assembly is designed so that the resonance frequency of the system is at least two orders of magnitude greater than the maximum HFOV driving signal frequency. This design, and the use of the sinusoidal driving signal, prevents the excitation of resonances in the piston 60 and seal. This further decreases the vibration and noise associated with the operation of the ventilator pump 20.

The output of the ventilator pump 20 is controlled either by setting the amplitude of the delivered pressure or of the tidal volume, as further described below, where the choice of which variable can be determined by the operator of the computer 34. The actual pressure measured by the pressure transducer 36 alone could be the controlled variable whereby the computer 34 maintains a predetermined pressure by controlling the ventilator pump 20 in this case. The pressure transducer 38 would not be necessary. If the tidal volume or delivered pressure is chosen as the controlled variable, the signals from the pressure transducers 36 and 38 are received by the computer 34, and the computer 34 computes the tidal volume or delivered pressure for each oscillation of the piston 60. The only restrictions on the pressure measurements are that they must have an adequate frequency response and must not significantly increase the dead space between the fresh gas into the bias flow inlet 26 and the exhaust out of the exhaust outlet 28 and the tube 30. The pressure transducers 36 and 38 should present as small a pressure drop to the patient circuit P as possible.

The mean pressure inside of the patient circuit P maintains the lung of the patient or subject at a desired mean lung volume. If the mean pressure were transmitted to the piston 60 of the ventilator pump 20, the resulting displacement of the piston 60 would have to be countered by a DC current through the coil 74. The magnitude of the DC current required to counter the expected maximum mean pressure is much higher than the alternating current provided by the pump drive 40 required to drive the piston 60, and thus puts an unacceptable requirement on the design of the coil 74.

Thus, the flexible diaphragm 106 between the pump piston 60 and outlet 116 of the ventilator pump 20 blocks the transmission of the pressure to the piston 60. Phantom lines 106a show a position of the diaphragm 106 as deflected when air pressure develops in the patient circuit P thereby enlarging the cavity 112. The diaphragm 106 preferably does not allow gas communication between the patient circuit P and the cavity 114 so that gas does not escape from the patient circuit P to the cavity 114. The mean pressure within the patient circuit P is thus maintained. When the diaphragm 106 is deflected as shown, the cavity 114 decreases, but preferably includes a slow leak to the external air so that air pressure does not build up within the cavity 114. The slow air leak is preferably between the piston 60 and the bolts 62 or the metal center support 70, although other means such as a pinhole in the cylinder wall 104b or the piston 60 would suffice. The slow leak acts as a low pass filter, being too slow to pass tidal volumes at the desired frequency of operation, yet allows any gas displaced by the diaphragm within the cavity 114 to escape through the slow leak. In this manner, the diaphragm 106 isolates or separates the source of the tidal volume oscillations, the piston 60, from the patient circuit P thereby blocking the mean airway pressures in the patient circuit P from the piston 60. This allows the coil 74 to be designed within acceptable design constraints.

The diaphragm 106, however, allows the transmission of the oscillating pressure generated by the piston 60 to be passed to the patient circuit P through the outlet 116. Phantom lines 106b show a position of the diaphragm 106 representing the amount of deflection due to the piston 60 generating tidal volumes when there is no air pressure bias in the patient circuit P. The diaphragm 106 thus deflects to a resting position due to mean pressure from the patient circuit P, and oscillates in response to movement of the piston 60. The amplitude and frequency response of the diaphragm 106 is designed to be adequate over the range of amplitudes and frequencies for which the ventilator V has been designed, as readily determinable by those skilled in the art. The initial size of the cavities 112 and 114 is determined, in part, by the elasticity of the diaphragm 106. The thickness and tension in the diaphragm 106 are chosen so that the frequency and amplitude response are not degraded and the deformation of the diaphragm 106 under mean pressure is not so great as to require inordinately large cavities 112 and 114.

To minimize the loss of tidal volume delivered to the subject through expansion of the walls of the patient circuit P, the compliance of the patient circuit P is minimized. Typically in prior HFOVs, the tidal volume is much smaller than the volume lost to wall expansion when the usual compliant patient circuit P is used. Thus, the hose 21, the water trap section 140, the tube 22, the bias flow section 24 and the tube 30 are designed with low compliance materials resulting in little or no expansion under typical airway pressures. However, for safety and ease of operation, the patient circuit P is flexible since otherwise moving the ventilator V would present a danger of injuring or extubating the subject by moving the endotracheal tube 32.

Figure 4:
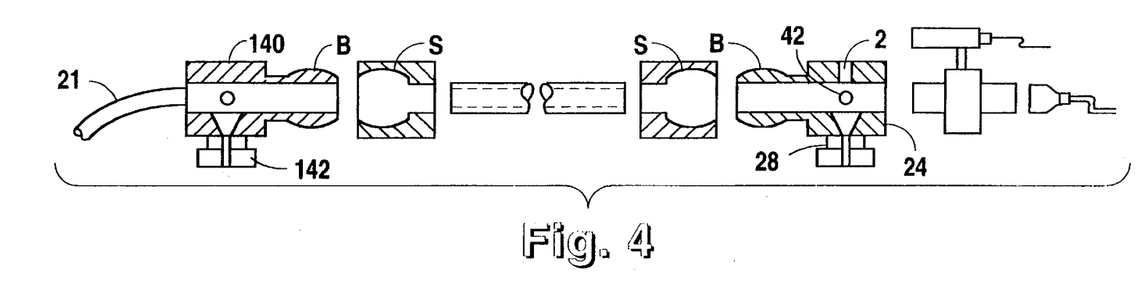
FIG. 4 is a partial diagram of the patient circuit of FIG. 1 illustrating a ball and socket construction.

Referring now to FIG. 4, a partial diagram of the patient circuit P is shown which is designed to include a series of ball B and socket S connectors that allow for free movement within a reasonable range of either the ventilator V or the subject without moving the other. In this manner, when the ball sections B are inserted into the socket sections S, the overall patient circuit P is relatively flexible allowing it to be moved relative to the subject, whereas the patient circuit P remains relatively non-compliant. The water trap section 140 includes a water trap 142 which is placed at a low spot in the patient circuit P so that water collecting in the patient circuit P can be drained, generally operating by gravity feed.

Figure 5:
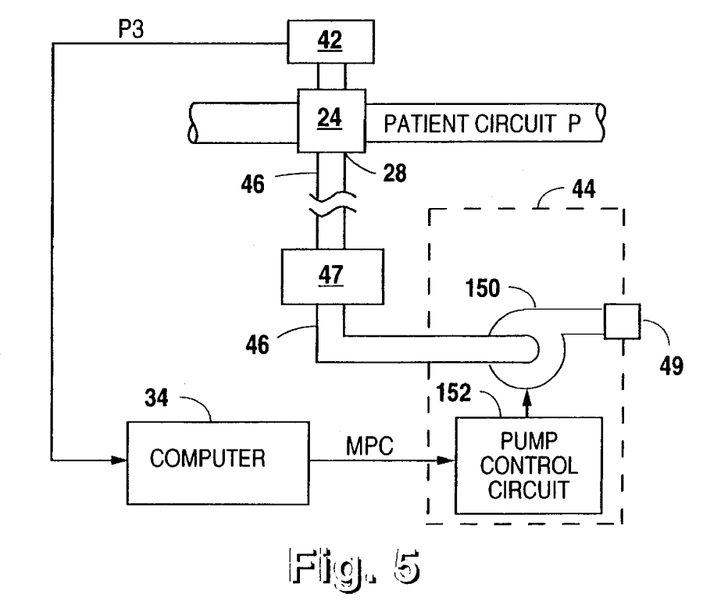
FIG. 5 is a block diagram illustrating the mean pressure control system of FIG. 1.

Referring now to FIG. 5, a block diagram of the mean pressure control system 44 is shown connected to the computer 34 and to the bias flow section 24. To minimize the loss of tidal volume through the exhaust outlet 28, the ventilator V of the present invention uses small, high resistance exhaust outlets 28 which require a consequent increase in the pressure drop across the exhaust outlet 28. The mean pressure should be independent of changes in other operating parameters of the ventilator V. Control of the mean pressure is complicated by the requirement of varying fresh gas or bias flow into the patient circuit P, since changes in the bias flow could otherwise change the mean pressure. Typically, a mixer (not shown) combines air and oxygen and provides this fresh air supply to the ventilator V through the bias flow inlet 26. Increasing or decreasing the fresh air supply into the patient circuit P would normally lead to an undesirable change in the mean pressure.

The mean pressure control system 44 includes a vacuum pump 150 to increase the pressure differential driving the exhaust flow out of the exhaust 28. The series of cavities 47 and tubes 46 act as an acoustic low pass filter. This filter action minimizes the transmission of oscillations from the vacuum pump 150 to the patient circuit P and, at the same time, minimizes the loss of tidal volume oscillations through the exhaust outlet 28. The mean pressure in the patient circuit P is monitored and analyzed by the computer 34 through the P3 signal provided by the mean airway pressure transducer 42. The computer 34 regulates the operation of the vacuum pump 150 through a pump control circuit 152 to maintain an operator-determined mean pressure in the patient circuit P to a predetermined level. Thus, as the mean pressure in the patient circuit P tends to increase or decrease, the computer 34 increases or decreases, respectively, the operation of the vacuum pump 150 thereby opposing the change in mean pressure.

Acoustic input impedance is used as a measure of the mechanical properties of the respiratory system. Lumped parameter models of the respiratory system are used to determine the values of respiratory system resistance and compliance, as well as more sophisticated measures of mechanical components of the lungs. The input impedance is measured, as described below, over a frequency band that may cover several hundred Hz, depending on the size of the lungs and parameters of interest. The mechanical properties of the respiratory system of the subject are then analyzed to determine the proper pressure and tidal volume to deliver to the subject by the ventilator V. Thus mean pressure and controlled variable, either delivered pressure or tidal volume, are determined and input to the computer 34, and the subject is then placed on the ventilator V. The respiratory mechanical properties are periodically measured during the ventilation, and the control variables are updated in the computer 34 accordingly. A separate measurement system may be used to measure the input impedance of the respiratory system, as will be described below, although the ventilator V, equipped with the pressure transducers, 36 and 38, is capable of making the measurements in situ and in vivo using the four-pole acoustic modelling technique described below.

Figure 6:
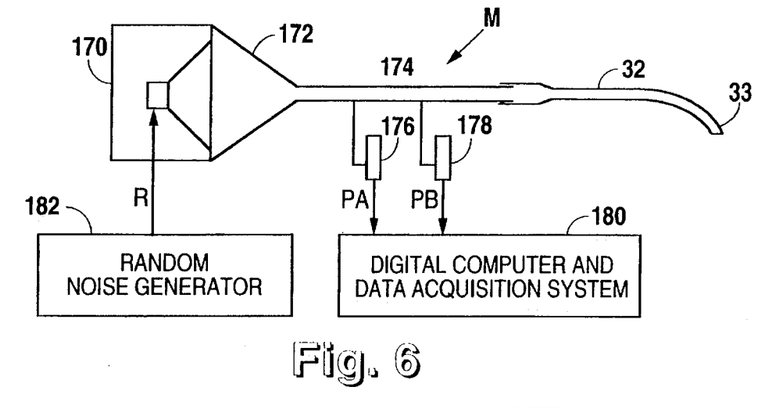
FIG. 6 in a simplified block diagram of a forced oscillation system according to the present invention which is used to measure mechanical properties of the respiratory system.
Figure 7:
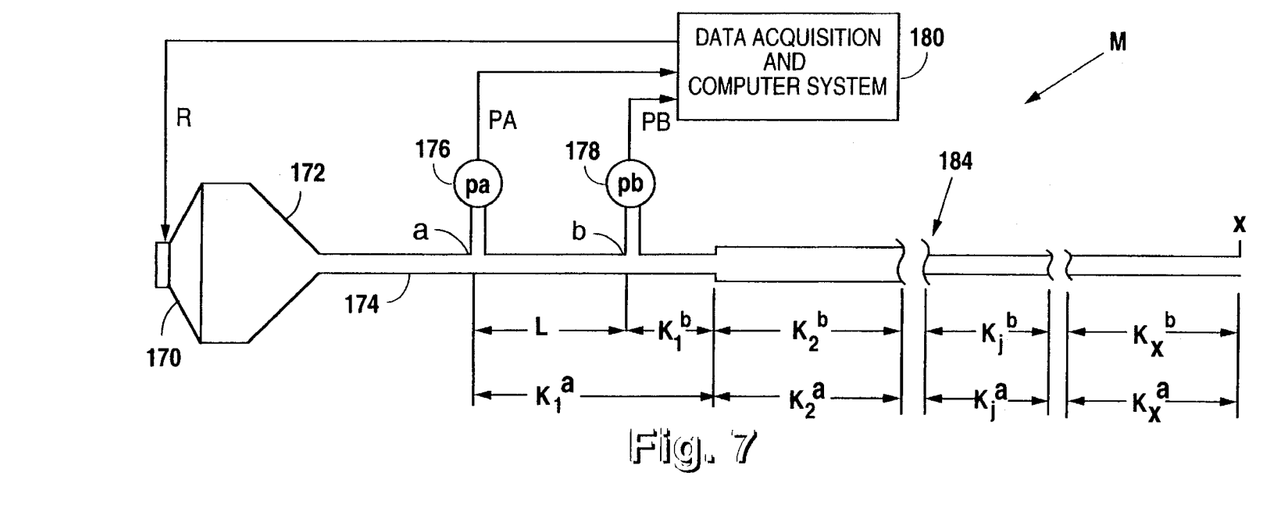
FIG. 7 is a diagram showing an alternate embodiment of the measuring system of FIG. 6, also showing a schematic representation of the endotracheal tube and respiratory system.

Referring now to FIG. 6, a simplified block diagram of a forced oscillation system according to the present invention, generally referred to by the letter M, is shown which allows in situ and in vivo measurement of the input impedance and compliance of the respiratory system. A loudspeaker 170 is used to generate a random tidal volume for purposes of measurement. A funnel 172 is connected between the loudspeaker 170 and a suitable tube 174, the funnel 172 serving to channel the tidal volume from the loudspeaker 170 to the tube 174. Two flow meter pressure transducers 176 and 178, similar to the pressure transducers 36 and 38, are attached to the tube 174 located a known distance L apart. The pressure transducers 176 and 178 measure the pressure in the tube 174 at their respective locations and convert the measured pressures to voltage signals PA and PB which are provided to a data acquisition and computer system 180. A random noise generator 182 provides a signal R to the loudspeaker 170. Alternatively, the computer system 180 could provide the random noise voltage signal R to the loudspeaker 170 (FIG. 7). The endotracheal tube 32, is connected to the other end of the tube 174, and is used to intubate a subject whose respiratory system is to be measured.

The R signal is preferably frequency band limited to a range between 0.1 to 100 or 200 Hz, having an amplitude with a predetermined root mean square (RMS) level. The amplitude of the R signal may further be limited to predetermined maximum excursions or deviation values from the RMS level. Although the R signal is not completely random, these constraints are desirable for practicable purposes of measuring the input impedance of the respiratory system.

In this approach, the acoustics of the tubing system downstream, towards the subject, of the two pressure test points are modeled using four-pole acoustic elements. FIG. 7 shows an alternate embodiment of the measurement setup M of FIG. 6, the only difference being that the digital computer and acquisition system 180 is used to generate the R signal. FIG. 7 also shows a schematic representation of the endotracheal tube 32 modelled as a series of x segments of tubing of varying geometry and acoustic characteristics, shown generally as 184. The transducers 176 and 178 are connected at points a and b, respectively, separated by the known distance L.

The K parameters referred to in FIG. 7 are the four-pole acoustic elements of each segment of the system, where $[K^i]=[K_1{}^i][K_2{}^i]\ldots[K_j{}^i]\ldots[K_x{}^i]$ and $[K^i{}_j]$ is the four-pole acoustic element of the jth segment of the system, and i represents the starting point of the first segment. Referring to FIG. 7, $[K^a]$ is the four-pole characteristic of the tube 174 and the endotracheal tube 32 from the point a to the output x, and equals $[K_1{}^a][K_2{}^a]\ldots[K_j{}^a]\ldots[K_x{}^a]$ and $[K^b]$ is the four-pole characteristic of the tube 174 and the endotracheal tube 32 from the point b to the output x, and equals $[K_1{}^b][K_2{}^b]\ldots[K_j{}^b]\ldots[K_x{}^b]$. Each $[K^i{}_j]$ is a 2×2 matrix computed from standard acoustic models based on the geometry and elastic properties of the endotracheal tube 32, as well as the acoustic properties of the gas filling the tube, which can be entered into the memory of the data acquisition and computer system 180. Recall that the size, shape and material of the endotracheal tube 32 may vary. These differences are reflected in the $[K^i]$ characteristics. The four-pole acoustic modelling technique is generally known to those skilled in the art, as more full described in To, C. W. S. and Doige, A. G., A Transient Testing Technique for the Determination of Matrix Parameters of Acoustic Systems, I: Theory and Principles, Journal of Sound and Vibration, Vol. 62(2), pgs. 207–222 (1979), and To, C. W. S. and Doige, A. G., A Transient Testing Technique for the Determination of Matrix Parameters of Acoustic Systems, II: Experimental Procedures and Results, Journal of Sound and Vibration, Vol. 62(2), pgs. 223–233 (1979). See also Seybert, A. F. and Ross, D. F., Experimental determination of acoustic properties using a two-microphone random excitation technique, J. Acous. Soc. Am., 61(5), 1977.

The pressure transducers 176 and 178 measure the time-varying pressures at the two locations a and b in the tube 174 over one inspiratory cycle. The power spectral densities of the time varying pressure signals are preferably estimated using fast Fourier transform, although other equivalent techniques could be used. The estimates of the power spectral densities can be improved by averaging over more than one inspiratory cycle. The pressure and volume flow spectra, $P_x$ and $U_x$, at the output 33 of the endotracheal tube 32 as represented by the last segment x, can be computed using equation 1:

$$\begin{bmatrix} P_i \\ U_i \end{bmatrix} = [K^i] \begin{bmatrix} P_x \\ U_x \end{bmatrix} \quad (1)$$

where Pi and Ui are the pressure and volume flow spectra at point i, where a and then b is substituted for i, respectively. For pressure measurements at any two points, equation (1) reduces to a system of four equations in four unknowns: $U_a$, $U_b$, $P_x$ and $U_x$. This system of equations can then be solved for $U_x$, the power spectral density of the volume flow at the last segment x which is the outlet 33 of the endotracheal tube 32. Also, Px can be readily solved in a similar fashion. The input impedance of the respiratory system is defined as the ratio $P_x/U_x$ which is a complex number.

If delivered pressure and tidal volume are to be measured only at a given frequency, the R signal need only be sinusoidal and not random. The inverse Fourier transform of $U_x$ provides $u_x(t)$, the time varying tidal volume flow. Integrating the time varying volume flow $u_x(t)$ over one inspiratory cycle gives the tidal volume, referred to as $V_T$, inspired during that inspiratory cycle. Similarly, the inverse Fourier transform of $P_x$ provides $p_x(t)$, the time varying pressure, and integrating over one inspiratory cycle gives the delivered pressure $P_D$ during the inspiratory cycle. If x is located at the end of the endotracheal tube 32, the computed $V_T$ or $P_D$ is the tidal volume or pressure delivered to the patient, respectively. This method can be applied over an interval of breaths to provide a periodically updated measurement of delivered tidal volume or pressure.

In summary, the four-pole acoustic elements relate the time-varying pressure and velocity at one location to the dynamic pressure and velocity at a different location. This four-pole approach to the acoustic modeling allows realistic tubing of varying acoustic characteristics to be accurately modelled. Elements for straight sections, contractions and expansions are readily available in literature. The measured transfer function between the pressure transducers 176 and 178 at the test locations a and b are expressed in terms of the unknown input impedance and the tubing four-pole parameters. Algebraic manipulation of the complex valued equation results in a solution for the end impedance.

The four-pole method can accurately account for the effect of the endotracheal tube 32 connecting the ventilator V to the patient. This is a major advantage over previous methods of computing respiratory system input impedance for intubated patients. Previously, the input impedance of the endotracheal tube 32 was assumed to act as a linear impedance in series with the respiratory system impedance, although this assumption becomes erroneous as the frequency increases.

The four-pole method described above can also be used to compute the unsteady pressure amplitude distal to the endotracheal tube 32. The proximal pressure is easily measured and used to provide an indication of the pressure being delivered to the patient. However, as noted above, the presence of the endotracheal tube 32 can severely distort the proximal pressure measurement during high frequency ventilation.

The computer 34 can be programmed to provide band limited, random noise on the VPC signal similar to the R signal, which is one excitation method that can be used to measure the respiratory mechanical parameters, such as input impedance and compliance. The ventilator V can generate band-limited, random-noise at arbitrary airway pressures due to the action of the flexible diaphragm 106, allowing the measurement of lung mechanical parameters without requiring a change in lung volume.

The input impedance of the patient connected to the ventilator can be measured using the measurement system M, as described above or by the ventilator V. The geometry and elastic properties of the endotracheal tube 32 can be entered into the memory of the computer 34 of the ventilator V prior to the patient being placed on the ventilator V. Measurements of the proximal pressures can then be used as input to an algorithm incorporating the four-pole method to compute the amplitude of the pressure delivered $P_D$ to the patient. This method would allow for the rapid, on-line and continuous calculation of the peak pressures delivered to the patient by the ventilator V. Likewise, rapid, on-line and continuous calculation of the delivered tidal volume $V_T$ can be made by the computer 34 and controlled by manipulating the VPC signal provided to the pump driver 40. The computer 34 can thus control the ventilator pump 20 to maintain either the tidal volume or pressure delivered to the subject.

Although the method and apparatus of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

What is claimed is:

1. A ventilator apparatus for providing assistance in breathing to a living subject, comprising:

a low compliance patient circuit tube having a first end and a second end;

means mounted to said patient circuit tube for providing fresh gas into said patient circuit tube and for exhausting exhaled gas out of said patient circuit tube;

an endotracheal tube intubated in the subject coupled to said first end of said patient circuit tube;

a pump for generating tidal volumes having an outlet coupled to said second end of said patient tube, said pump further comprising, a closure having a cavity area, said closure including said pump outlet and an opening for communication with said cavity area, a piston and a rolling seal covering said opening, said piston and said rolling seal allowing a relatively slow leak from said cavity area, means for oscillating said piston, and a flexible membrane provided within said cavity area between said pump outlet and said piston, said membrane dividing said cavity area into a first cavity between said membrane said outlet and a second cavity between said membrane and said piston, said membrane preventing communication of gas between said tube and said second cavity; and wherein gas pressure developed in said patient circuit tube communicates to said first cavity deflecting said membrane towards said second cavity, wherein gas displaced by said membrane displacement in said second cavity escapes through said slow leak, wherein when said oscillating means oscillates said piston, said flexible membrane oscillates correspondingly generating tidal volumes through said patient circuit tube and said endotracheal tube.

2. The ventilator apparatus of claim 1, wherein said oscillating means includes a magnet and coil assembly.

3. The ventilator apparatus of claim 1, further comprising:

a pressure transducer mounted on said patient circuit tube relatively near said endotracheal tube; and means coupled to said pressure transducer and said oscillating means for maintaining the mean value of said measured pressure at a predetermined level.

4. The ventilator apparatus of claim 3, wherein said maintaining means includes a digital computer.

5. The ventilator apparatus of claim 1, wherein said flexible membrane comprises latex.

6. A ventilator apparatus for providing assistance in breathing to a living subject, comprising:

a low compliance patient circuit tube having a first end and a second end;

bias flow means mounted to said patient circuit tube having an inlet for providing fresh gas into said patient circuit tube and an exhaust outlet for exhausting exhaled gas from said patient circuit tube;

pumping means coupled to said first end of said patient circuit tube for generating tidal volumes;

an endotracheal tube mounted to said second end of said patient circuit tube and intubated in the subject;

a first pressure transducer mounted on said bias flow means for measuring pressure within said patient circuit tube;

means coupled to said bias flow means for minimizing any transmission of oscillations to said patient circuit tube;

means coupled through said means for minimizing to said bias flow means exhaust outlet for varying said pressure within said patient circuit tube; and means coupled to said means for varying said pressure and said first pressure transducer for controlling said varying means to maintain a predetermined mean value of said pressure.

7. The ventilator apparatus of claim 6, wherein said means for varying said pressure includes a vacuum pump.

8. The ventilator apparatus of claim 7, wherein said means for varying said pressure includes a series of cavities and tubes coupled between said bias flow means exhaust outlet and said vacuum pump.

9. The ventilator apparatus of claim 6, wherein said controlling means includes a digital computer.

10. The ventilator apparatus of claim 6, further comprising:

a second pressure transducer mounted on said patient circuit tube relatively near said endotracheal tube for measuring delivered pressure; and wherein said controlling means is coupled to said second pressure transducer and said pumping means and controls said pumping means to maintain said measured delivered pressure at a predetermined level.

11. The ventilator apparatus of claim 6, wherein said pumping means comprises:

a pump having a piston and an outlet coupled to said first end of said patient circuit tube;

a flexible membrane mounted within said piston pump between said piston and said pump outlet for isolating said piston from said pressure within said patient circuit tube.

12. The ventilator apparatus of claim 11, wherein said flexible membrane comprises latex.

13. An apparatus for measuring the mechanical properties of the respiratory system of a living subject, comprising:

a patient circuit tube having a first end and a second end;

a first pressure transducer mounted at a first location a on said patient circuit tube for measuring the pressure within said patient circuit tube at said first location a;

a second pressure transducer mounted at a second location b on said patient circuit tube for measuring the pressure within said patient circuit tube at said second location b, said second location b being a predetermined length from said first location a;

an endotracheal tube intubated in the subject having an input coupled to said second end b of said patient circuit tube, and an output represented as x, said patient circuit tube and said endotracheal tube having a known four-pole acoustic characteristic $[K^a]$ between said first location a and said output x, said patient circuit tube and said endotracheal tube having a known four-pole acoustic characteristic $[K^b]$ between said second location b and said output x, pumping means mounted to said first end of said patient circuit tube having an input for oscillating said pumping means according to a signal received on said input;

a random noise generator for providing a frequency band limited random signal to said pumping means input;

means coupled to said first and second pressure transducers for monitoring the measured pressures at said first location a and said second location b during each inspiratory cycle, for determining the power spectral densities $P_a$ and $P_b$ of the pressures at said first location a and said second location b, respectively, using fast Fourier transform, and for calculating $U_a$, $U_b$, $P_x$ and $U_x$ from the following equations:

$$\begin{bmatrix} P_a \\ U_a \end{bmatrix} = [K^a] \begin{bmatrix} P_x \\ U_x \end{bmatrix}$$

$$\begin{bmatrix} P_b \\ U_b \end{bmatrix} = [K^b] \begin{bmatrix} P_x \\ U_x \end{bmatrix}$$

where $P_x$ is the power spectral density of the pressure at said output x of said endotracheal tube, and $U_a$, $U_b$ and $U_x$ are the power spectral densities of volume flow at said first location a, said second location b and said endotracheal tube output x, respectively.

14. The apparatus of claim 13, wherein said pumping means comprises a loudspeaker.

15. The apparatus of claim 13, wherein said random signal is frequency band limited between approximately 0.1 Hertz to approximately 200 Hertz having a predetermined root mean square amplitude.

16. The apparatus of claim 13, wherein said monitoring, determining and calculating means comprises a digital computer.

17. The apparatus of claim 16, wherein said digital computer provides said random signal.

18. A ventilator apparatus for providing assistance in breathing to a living subject, comprising:

a patient circuit tube having a first end and a second end;

bias flow means mounted on said patient circuit tube for providing fresh gas into and for exhausting exhaled gas out of said patient circuit tube;

a first pressure transducer mounted at a first location a on said patient circuit tube for measuring pressure within said patient circuit tube at said first location a;

a second pressure transducer mounted at a second location b on said patient circuit tube for measuring pressure within said patient circuit tube at said second location b, said second location b being a predetermined distance from said first location a;

an endotracheal tube intubated in the subject having an input coupled to said second end of said patient circuit tube, and an output represented as x, said patient circuit tube and said endotracheal tube having a known four-pole acoustic characteristic $[K^a]$ between said first location a and said output x, said patient circuit tube and said endotracheal tube having a known four-pole acoustic characteristic $[K^b]$ between said second location b and said output x;

pumping means having an outlet coupled to said first end of said patient circuit tube for generating sinusoidal tidal volumes;

means coupled to said first and second pressure transducers and to said pumping means for monitoring said measured pressures at said first location a and said second location b over each inspiratory cycle, for determining the power spectral densities $P_a$ and $P_b$ of the measured pressures at said first location a and second location b, respectively, using fast Fourier transform, for calculating $U_x$ from the following equations:

$$\begin{bmatrix} P_a \\ U_a \end{bmatrix} = [K^a] \begin{bmatrix} P_x \\ U_x \end{bmatrix}$$

$$\begin{bmatrix} P_b \\ U_b \end{bmatrix} = [K^b] \begin{bmatrix} P_x \\ U_x \end{bmatrix}$$

where $P_x$ is the power spectral density of the pressure at said output x of said endotracheal tube, and $U_a$, $U_b$ and $U_x$ are the power spectral densities of volume flow at said first location a, said second location b and said endotracheal tube output x, respectively, and for calculating the delivered tidal volume $V_T$ for each inspiratory cycle at said output x by solving for $U_x$, calculating the inverse Fourier transform of $U_x$ to determine the volume flow $u_x(t)$ at said output x and integrating the volume flow $u_x(t)$ over each inspiratory cycle; and     wherein said monitoring, determining and calculating means controls said pumping means to maintain the delivered tidal volume $V_T$ at a predetermined level.

19. The breathing apparatus of claim 18, wherein said monitoring and calculating means calculates the delivered pressure $P_D$ at said output x by solving for $P_x$, calculating the inverse Fourier transform of $P_x$ to determine pressure $p_x(t)$ at said output x, and the maximum and minimum pressure $P_D$ max and $P_D$ min over each inspiratory cycle at said output x; and     wherein said monitoring, determining and calculating means controls said pumping means to maintain the maximum delivered pressure $P_D$max, rather than said delivered tidal volume $V_T$, at a predetermined level.

20. The ventilator apparatus of claim 18, wherein said monitoring, determining and calculating means comprises a digital computer.

21. The ventilator apparatus of claim 18, wherein said pumping means includes a piston and a magnet and coil assembly.

22. The ventilator apparatus of claim 21, wherein said pumping means further includes a flexible membrane for isolating the pressure in said patient circuit tube from said piston.

23. The ventilator apparatus of claim 18, further comprising:

said monitoring, determining and calculating means includes means for providing a frequency band limited random signal to said pumping means, and calculates the input impedance of the respiratory system defined as $P_x/U_x$.

24. The ventilator apparatus of claim 18, further comprising:

a pressure transducer mounted on said bias flow means for measuring pressure within said bias flow means;

said bias flow means including an exhaust outlet for exhausting said exhaled gas;

means coupled to said bias flow means exhaust outlet for varying the pressure within said bias flow mean; and     wherein said monitoring, determining and calculating means is coupled to said bias flow means pressure transducer and said means for varying said pressure within said bias flow means, and controls said varying means to maintain the mean value of said pressure at a predetermined level.

25. The ventilator apparatus of claim 24, wherein said monitoring, determining and calculating means comprises a digital computer.

\* \* \* \* \*

UNITED STATES PATENT AND TRADEMARK OFFICE
CERTIFICATE OF CORRECTION

PATENT NO.    : 5,555,880
DATED         : September 17, 1996
INVENTOR(S)   : Dean C. Winter, Ralph E. Harris and Kevin S. Honeyager

It is certified that error appears in the above-identified patent and that said Letters Patent is hereby corrected as shown below:

Column 1,
Line 5, please insert the following statement before the FIELD OF INVENTION:
-- STATEMENT REGARDING FEDERALLY SPONSORED RESEARCH       This invention was made with government support under Contracts Numbered DADA 11-90-P-6527, DADA 11-90-M-0267, DADA 11-89-P-1471, and DADA 11-89-M-1785 awarded by the United States Army Institute of Surgical Research. The United States Government has certain rights to this invention. --

Signed and Sealed this

Twenty-third Day of March, 2004

JON W. DUDAS
*Acting Director of the United States Patent and Trademark Office*